United States Patent
Hatano et al.

(10) Patent No.: US 11,304,593 B2
(45) Date of Patent: Apr. 19, 2022

(54) MEDICAL APPARATUS

(71) Applicant: OLYMPUS CORPORATION, Tokyo (JP)

(72) Inventors: Keisuke Hatano, Koganei (JP); Yutaro Watanabe, Chofu (JP)

(73) Assignee: OLYMPUS CORPORATION, Tokyo (JP)

( * ) Notice: Subject to any disclaimer, the term of this patent is extended or adjusted under 35 U.S.C. 154(b) by 385 days.

(21) Appl. No.: 16/401,138

(22) Filed: May 2, 2019

(65) Prior Publication Data

US 2019/0254503 A1    Aug. 22, 2019

Related U.S. Application Data

(63) Continuation of application No. PCT/JP2017/037074, filed on Oct. 12, 2017.

(30) Foreign Application Priority Data

Dec. 27, 2016 (JP) .............................. JP2016-253904

(51) Int. Cl.
*A61B 1/005* (2006.01)
*A61B 1/00* (2006.01)
*A61B 34/00* (2016.01)

(52) U.S. Cl.
CPC .............. *A61B 1/0052* (2013.01); *A61B 1/00* (2013.01); *A61B 1/0057* (2013.01);
(Continued)

(58) Field of Classification Search
CPC .... A61B 2017/003; A61B 2017/00318; A61B 2017/00323; A61B 2017/00327;
(Continued)

(56) References Cited

U.S. PATENT DOCUMENTS 4,893,613 A * 1/1990 Hake .................... A61B 1/0053
                                                600/144
6,523,428 B2 * 2/2003 Kaji ........................ F16J 3/043
                                                74/18.1
(Continued)

FOREIGN PATENT DOCUMENTS

EP    1946694 A1    7/2008
EP    2050383 A1    4/2009
(Continued)

OTHER PUBLICATIONS

International Search Report dated Dec. 19, 2017 issued in PCT/JP2017/037074.

*Primary Examiner* — Ryan N Henderson
(74) *Attorney, Agent, or Firm* — Scully, Scott, Murphy & Presser, P.C.

(57) ABSTRACT

A medical apparatus includes: an operation portion; an annular wall portion including a base portion connectedly provided to an exterior case and a protruding end portion; an operation lever configured to be tilted by an operator; a cover member including a first fitted portion fitted to the operation lever, a deforming portion configured to deform accompanying a tilt of the operation lever, and a second fitted portion with an inner circumferential surface fitted to an outer circumferential surface of the wall portion; and an elastic member including a contact portion in contact with an outer circumferential surface of the second fitted portion, the contact portion being fixed to the exterior case and being deformed to press the outer circumferential surface of the second fitted portion.

7 Claims, 3 Drawing Sheets

(52) U.S. Cl.
CPC ...... *A61B 1/00066* (2013.01); *A61B 1/00147* (2013.01); *A61B 2034/742* (2016.02)

(58) Field of Classification Search
CPC ... A61B 34/74; A61B 2034/742; A61B 1/005; A61B 1/0051; A61B 1/0052; A61B 1/0053; A61B 1/0055; A61B 1/0056; A61B 1/0057; A61B 1/0058; A61B 1/008; A61B 1/00066; A61B 1/00068; A61M 25/0133; A61M 25/0136; A61M 25/0147

See application file for complete search history.

(56) References Cited

U.S. PATENT DOCUMENTS

| | | | | |
|---|---|---|---|---|
| 8,578,808 | B2* | 11/2013 | Koitabashi | A61B 1/0052 74/471 XY |
| 8,840,544 | B2* | 9/2014 | Hosaka | G02B 23/2476 600/131 |
| 9,500,851 | B2* | 11/2016 | Yasunaga | G02B 23/2476 |
| 9,743,827 | B2* | 8/2017 | Yasunaga | A61B 1/0057 |
| 10,537,230 | B2* | 1/2020 | Sato | G02B 23/24 |
| 10,918,266 | B2* | 2/2021 | Hatano | A61B 1/0052 |
| 10,980,401 | B2* | 4/2021 | Hatano | A61B 1/00066 |
| 11,122,966 | B2* | 9/2021 | Ito | A61B 1/00066 |
| 2002/0050181 | A1* | 5/2002 | Kaji | F16J 3/043 74/18 |
| 2004/0193014 | A1* | 9/2004 | Miyagi | A61B 1/00039 600/146 |
| 2004/0267093 | A1* | 12/2004 | Miyagi | A61B 1/00039 600/146 |
| 2008/0207998 | A1* | 8/2008 | Maruyama | G02B 23/2476 600/114 |
| 2008/0275303 | A1* | 11/2008 | Koitabashi | G05G 5/04 600/146 |
| 2009/0149709 | A1* | 6/2009 | Koitabashi | A61B 1/00149 600/131 |
| 2012/0209067 | A1* | 8/2012 | Hosaka | A61B 1/0052 600/109 |
| 2016/0192823 | A1* | 7/2016 | Yasunaga | A61B 1/0052 600/109 |
| 2016/0227986 | A1* | 8/2016 | Yasunaga | A61B 1/0057 |
| 2016/0231556 | A1* | 8/2016 | Yasunaga | G01D 11/16 |
| 2017/0196435 | A1* | 7/2017 | Sato | G02B 23/2476 |
| 2018/0049625 | A1* | 2/2018 | Nakade | A61B 1/00071 |
| 2018/0317748 | A1* | 11/2018 | Hatano | G02B 23/2476 |
| 2019/0133419 | A1* | 5/2019 | Hatano | A61B 1/0052 |

FOREIGN PATENT DOCUMENTS

| | | | |
|---|---|---|---|
| EP | 3202302 A1 | 8/2017 | |
| JP | 2003-135385 A | 5/2003 | |
| JP | 2003135385 A * | 5/2003 | ......... G02B 23/2476 |
| JP | 2004-321612 A | 11/2004 | |
| JP | 2005-279119 A | 10/2005 | |
| WO | WO 2007/055163 A1 | 5/2007 | |
| WO | WO 2008/018554 A1 | 2/2008 | |
| WO | WO 2016/052147 A1 | 4/2016 | |

* cited by examiner

MEDICAL APPARATUS

CROSS REFERENCE TO RELATED APPLICATION

This application is a continuation application of PCT/JP2017/037074 filed on Oct. 12, 2017 and claims benefit of Japanese Application No. 2016-253904 filed in Japan on Dec. 27, 2016, the entire contents of which are incorporated herein by this reference.

BACKGROUND OF THE INVENTION

1. Field of the Invention

The present invention relates to a medical apparatus provided with an operation lever with which an operator can perform a tilt operation to an operation portion grasped by the operator.

2. Description of the Related Art

Recently, medical apparatuses, for example, endoscopes have been widely used in a medical field. With an endoscope used in the medical field, it is possible to, by inserting an elongated insertion portion into a body cavity, which is a subject, observe a site to be examined in the body cavity.

A configuration is well known in which a bending portion bendable, for example, in a plurality of directions is provided on a distal end side of the insertion portion of the endoscope.

The bending portion causes advanceability of the insertion portion in a bent part in the body cavity to be improved, and, in addition, causes an observation direction of an observation optical system provided on a distal end portion, which is located on a more distal end side than the bending portion on the insertion portion, to be changeable.

To give an example, one or two pairs of wires, that is, two or four wires the distal ends of which are fixed to the bending portion are inserted in the insertion portion of the endoscope and in the operation portion of the endoscope connectedly provided to a proximal end of the insertion portion.

Any of the four wires is pulled, accompanying a tilt operation of a bending operation member provided on the operation portion of the endoscope, for example, an operation lever of a known joystick device.

Consequently, the bending portion can bend one of two directions of up and down, or one of two directions of left and right, or one of four directions of up, down, left, and right.

A shaft body of the operation lever is extended outside the operation portion from inside of the operation portion through a cavity in an annular wall portion provided on an exterior case of the operation portion.

Note that a handler to be grasped by an operator when the shaft body is tilted by the operator is provided on an extended end, which is an end portion of the shaft body.

A configuration is well known in which a cover member is provided over the shaft body, the cover member being configured to, by covering the cavity in the wall portion, prevent entry of liquid, dust, and the like into the operation portion through the cavity.

The cover member is formed with rubber or the like in a sheet shape substantially concentrically with the shaft body, and the cover member has a deforming portion configured with an elastic member.

Japanese Patent Application Laid-Open Publication No. 2004-321612 discloses a configuration of an operation portion of an endoscope in which a first fitted portion connectedly provided to a deforming portion to be an inner circumferential edge of the deforming portion is fitted to an outer circumference of a shaft body, and a second fitted portion connectedly provided to the deforming portion to be an outer circumferential edge of the deforming portion is tightly fitted in a fixing hole or the like provided, for example, in an exterior case of the operation portion and fitted to an outer circumferential surface of a wall portion.

SUMMARY OF THE INVENTION

A medical apparatus according to an aspect of the present invention is provided with: an operation portion configured to be grasped by an operator; an annular wall portion including a base portion connectedly provided to an exterior case of the operation portion and a protruding end portion protrudingly provided from the base portion by a predetermined height; an operation lever extended outside the operation portion from inside the operation portion in an area covered by the wall portion and configured so that the operator can perform a tilt operation to the operation portion; a cover member including a first fitted portion fitted to the operation lever, a deforming portion connectedly provided to the first fitted portion and configured to deform accompanying a tilt of the operation lever, and a second fitted portion connectedly provided to the deforming portion, an inner circumferential surface of the second fitted portion being fitted to an outer circumferential surface of the wall portion; and an elastic member including a contact portion in contact with an outer circumferential surface of the second fitted portion, the contact portion being fixed to the exterior case and being deformed to press the outer circumferential surface of the second fitted portion.

DETAILED DESCRIPTION OF THE PREFERRED EMBODIMENT(S)

An embodiment of the present invention will be described below with reference to drawings. Note that it should be noticed that the drawings are schematic, and a relationship between thickness and width of each member, a thickness ratio among respective members and the like are different from actual ones; and, among the mutual drawings, parts having a different mutual dimensional relationship or ratio are, of course, included.

Note that, in the embodiment shown below, description will be made with an endoscope as an example of a medical apparatus.

Figure 1:
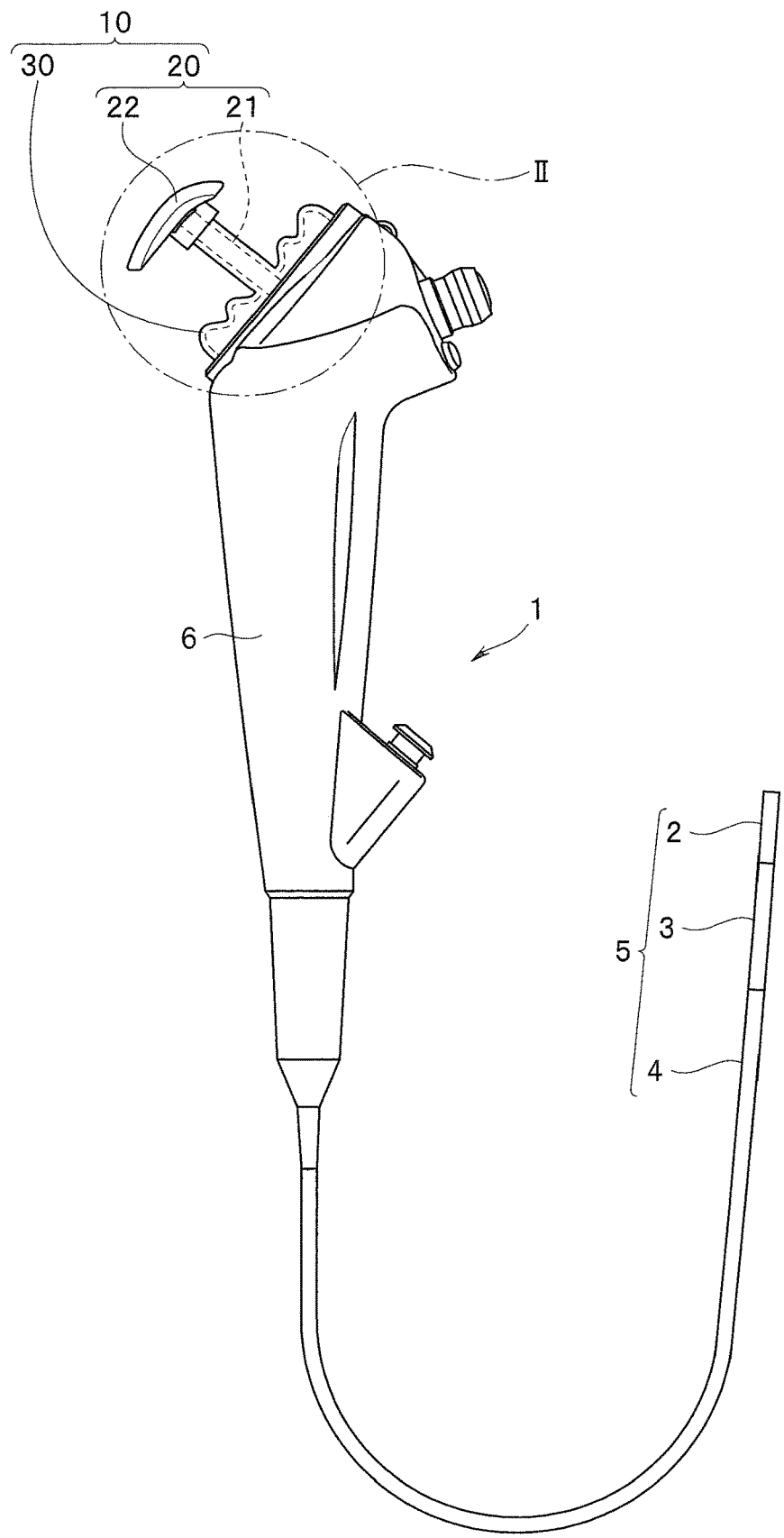
FIG. 1 is a perspective view of an endoscope of the present embodiment.

FIG. 1 is a perspective view of an endoscope of the present embodiment.

As shown in FIG. 1, a main part of an endoscope 1 is configured with an insertion portion 5 to be inserted into a subject and an operation portion 6 connectedly provided to a proximal end side of the insertion portion 5 and configured to be grasped by an operator.

Note that a universal cord not shown is extended from the operation portion 6, and the endoscope 1 is electrically connected to external apparatuses such as a control apparatus and an illumination apparatus via a connector not shown provided on an extended end of the universal cord.

The insertion portion 5 is configured being provided with a distal end portion 2, a bending portion 3, and a flexible tube portion 4 from a distal end side in that order and is formed in an elongated shape.

The bending portion 3 is bent in a plurality of directions, for example, four directions of up, down, right and left by a tilt operation of an operation lever 20 to be described later. The bending portion 3 thereby causes an observation direction of an observation optical system not shown that is provided in the distal end portion 2 to be changeable and causes insertability of the distal end portion 2 in a subject to be improved. Furthermore, the flexible tube portion 4 is connectedly provided to a proximal end side of the bending portion 3.

The operation portion 6 is provided with a bending operation mechanism 10 of the endoscope 1. A main part of the bending operation mechanism 10 is configured being provided with the operation lever 20 configured to cause the bending portion 3 to bend by an operator being able to perform a tilt operation of the operation lever 20 to the operation portion 6, and a seal unit 30.

The operation lever 20 is configured with a shaft body 21 and a handler 22 provided on an end portion of the shaft body 21.

Note that an end portion on an opposite side of the handler 22 of the shaft body 21 is connected to a device not shown, which is provided in the operation portion 6 and configured to cause the bending portion 3 to bend accompanying a tilt of the operation lever 20.

The shaft body 21 is extended outside the operation portion 6 from inside the operation portion 6 through a cavity 6v which is an area covered with an annular wall portion 40 connectedly provided to an exterior case 6k of the operation portion 6, which is to be described later (see FIG. 2 for the cavity 6v, the annular wall portion 40, and the exterior case 6k). The handler 22 is provided on an extended end of the shaft body 21 and located outside the operation portion 6.

Next, a configuration of the bending operation mechanism 10 will be described using FIGS. 2 and 3. FIG. 2 is a cross-sectional view showing the bending operation mechanism of the endoscope surrounded by a line II in FIG. 1 together with a part of the exterior case of the operation portion. FIG. 3 is a partial enlarged cross-sectional view showing a state in which a second fitted portion of a cover member is fitted into a fixing hole of the exterior case in FIG. 2.

Figure 2:
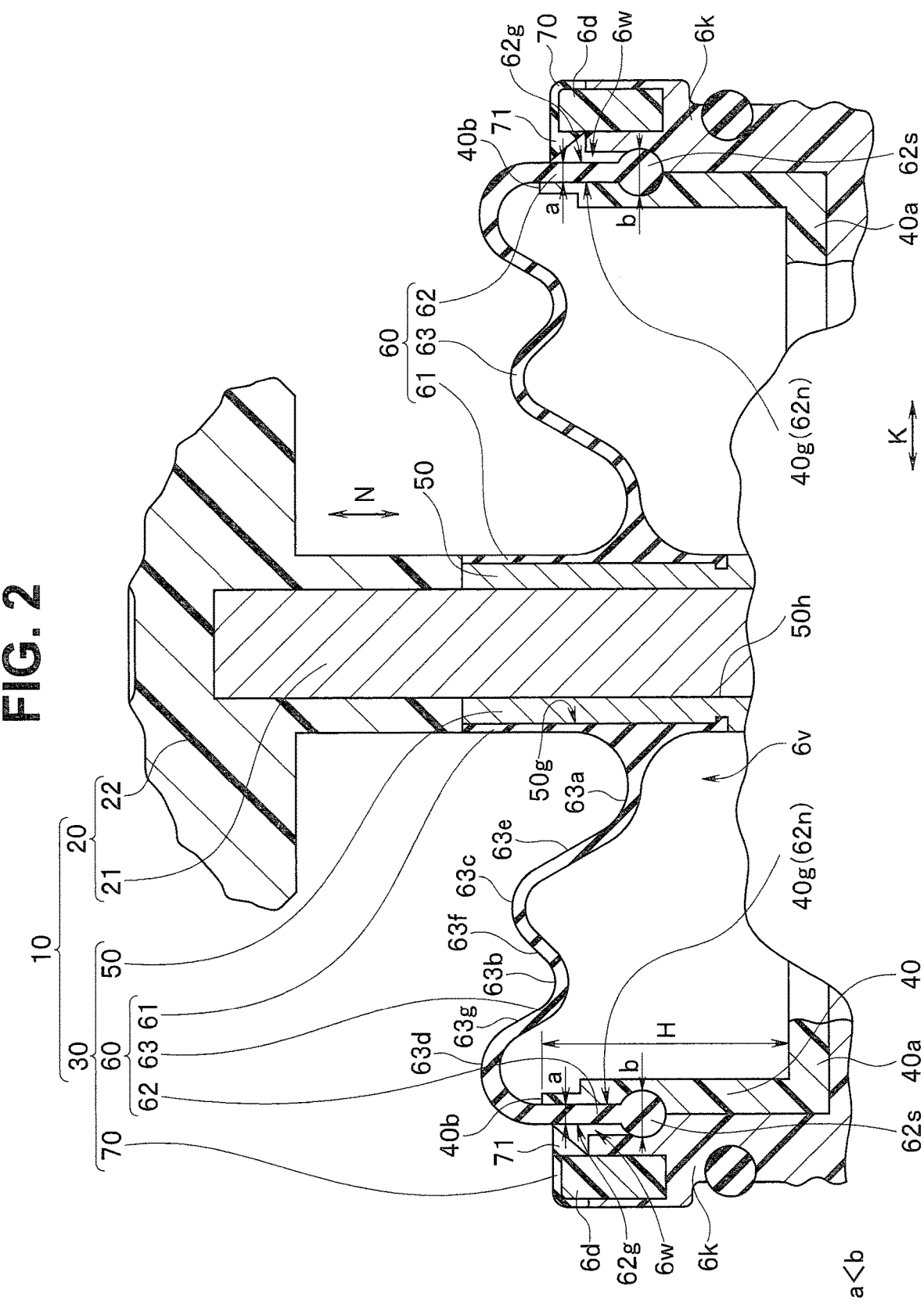
FIG. 2 is a cross-sectional view showing a bending operation mechanism of the endoscope surrounded by a line II in FIG. 1 together with a part of an exterior case of an operation portion.
Figure 3:
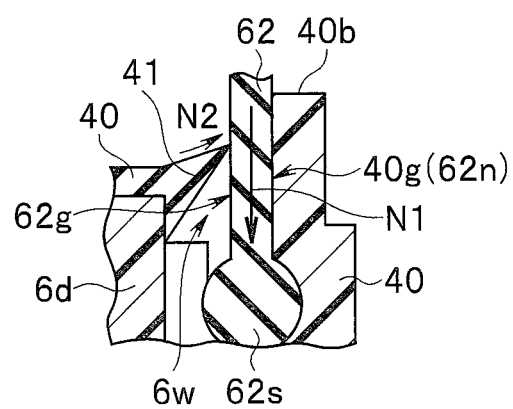
FIG. 3 is a partial enlarged cross-sectional view showing a state in which a second fitted portion of a cover member is fitted into a fixing hole of the exterior case in FIG. 2.

As shown in FIG. 2, the seal unit 30 prevents liquid, dust, and the like from entering the operation portion 6 via the cavity 6v to be described later by covering the cavity 6v.

The seal unit 30 is configured with a tubular member 50, a sheet-shaped cover member 60, and an elastic member 70.

The tubular member 50 has a cavity 50h into which the shaft body 21 is to be fitted, along a longitudinal direction N of the shaft body 21 and is configured with a material having rigidity, such as stainless steel.

The cover member 60 is, for example, formed with silicone rubber in a sheet shape with a thickness of, for example, 1 mm. The cover member 60 is integrally formed relative to the tubular member 50 by insert molding or the like.

Note that the material constituting the cover member 60 is not limited to silicone rubber. The thickness of the cover member 60 is not limited to 1 mm.

The cover member 60 is configured having a first fitted portion 61, the second fitted portion 62 and a deforming portion 63.

The first fitted portion 61 is circumferentially fitted and fixed to an outer circumference 50g of the tubular member 50 along the longitudinal direction N of the tubular member 50. That is, the cover member 60 is integrally formed with the tubular member 50 at the first fitted portion 61.

The deforming portion 63 deforms and moves accompanying a tilt of the operation lever 20. The deforming portion 63 is connectedly provided to the first fitted portion 61, and circumferentially extends from the first fitted portion 61 to an outer side of the cover member 60 in a radial direction K of the cover member 60, that is, on the second fitted portion 62 side substantially concentrically with the first fitted portion 61.

The deforming portion 63 is configured, for example, with a plurality of concave portions 63a and 63b, a plurality of convex portions 63c and 63d, a slope 63e connecting the concave portion 63a and the convex portion 63c, a slope 63f connecting the convex portion 63c and the concave portion 63b, and a slope 63g connecting the concave portion 63b and the convex portion 63d. Note that the number of concave portions, the number of convex portions, and the number of slopes are not limited to the numbers shown in FIG. 2.

The second fitted portion 62 is connectedly provided to the outer circumferential edge of the deforming portion 63 and fitted to an outer circumferential surface 40g of the annular wall portion 40 connectedly provided to the exterior case 6k of the operation portion 6.

More specifically, the wall portion 40 is annularly formed, having a base portion 40a connectedly provided to the exterior case 6k and a protruding end portion 40b protrudingly provided from the base portion 40a by a predetermined height H along the longitudinal direction N. The cavity 6v is formed along the longitudinal direction N in the area covered by the wall portion 40.

On an outer surface on a further outer side than the wall portion 40 of the exterior case 6k in the radial direction K, that is, on the elastic member 70 side in FIG. 2, a fixing hole 6w having a predetermined depth is formed along the longitudinal direction N. The second fitted portion 62 is fitted in the fixing hole 6w.

An inner circumferential surface 62n of the second fitted portion 62 is thereby fitted to the outer circumferential surface 40g of the wall portion 40 through the fixing hole 6w.

Note that watertightness of the cover member 60 against the wall portion 40 is secured at the second fitted portion 62.

More specifically, on the second fitted portion 62, a seal portion 62s thicker than other parts of the second fitted portion 62 (a<b) and configured to secure watertightness of the part by being caused to be in contact with the wall portion 40 is formed.

By the seal portion 62s being in contact with the outer circumferential surface 40g of the wall portion 40 in the fixing hole 6w, watertightness of the cover member 60 against the wall portion 40 is secured at the second fitted portion 62.

On an outer surface of the exterior case 6k, an annular rigid body 6d is fixed on an outer side relative to the fixing hole 6w in the radial direction K, and the elastic member 70 formed, for example, of silicone rubber, is fixed to the rigid body 6d in a manner of being exposed from the outer surface of the exterior case 6k.

Note that the material constituting the elastic member 70 is not limited to silicone rubber. The elastic member 70 is integrally formed relative to the rigid body 6d, for example, by insert molding.

The elastic member 70 has a contact portion 71 that is in contact with an outer circumferential surface 62g of the second fitted portion 62 in the fixing hole 6w, and the contact portion 71 is fixed to the rigid body 6d in a state of being deformed so as to press the outer circumferential surface 62g of the second fitted portion 62 to an inner side in the radial direction K.

More specifically, the contact portion 71 of the elastic member 70 is in contact with the outer circumferential surface 62g of the second fitted portion 62 on the base portion 40a side relative to the protruding end portion 40b of the wall portion 40 in the longitudinal direction N and presses the second fitted portion 62 against the wall portion 40.

The elastic member 70 thereby prevents a gap from appearing between the second fitted portion 62 and the exterior case 6k in an area on an opposite side of a tilt direction in the radial direction K, accompanying the deforming portion 63 being deformed and moved when the operation lever 20 is tilted, by the contact portion 71 coming into contact with the outer circumferential surface 62g of the second fitted portion 62 and pressing the second fitted portion 62 against the wall portion 40.

Therefore, since the elastic member 70 presses the second fitted portion 62, it is preferable that the elastic member 70 is formed harder than the cover member 60 to secure certain pressing force.

Further, the contact portion 71 tapers off from the base portion 40a side toward the protruding end portion 40b side in the longitudinal direction N and has a triangular cross section.

A reason is that, at the time of fitting the second fitted portion 62 into the fixing hole 6w in a direction N1 toward the base portion 40a side in the longitudinal direction N in assembly, an area of contact of the contact portion 71 with the outer circumferential surface 62g is minimal as shown in FIG. 3, and, therefore, it is easy to fit the second fitted portion 62 into the fixing hole 6w.

Furthermore, since the contact portion 71 that is in contact with the outer circumferential surface 62g faces the protruding end portion 40b side in the longitudinal direction N at the time of fitting the second fitted portion 62 into the fixing hole 6w, the gap between the contact portion 71 and the outer circumferential surface 62g is more difficult to appear. This is another reason.

Note that other components of the bending operation mechanism 10 are the same as before.

As described above, in the present embodiment, the elastic member 70 configured to press the outer circumferential surface 62g of the second fitted portion 62 fitted in the fixing hole 6w against the wall portion 40 is fixed on the outer side of the fixing hole 6w in the radial direction K on the exterior case 6k.

According to the above, even if the deforming portion 63 moves to the inner side in the radial direction K accompanying the operation lever 20 being tilted, the contact portion 71 of the elastic member 70 located in an area on an opposite side of the tilt direction of the operation lever 20 in the radial direction K presses the second fitted portion 62.

Consequently, in addition to the effect that a gap does not appear between the contact portion 71 and the second fitted portion 62, a part of the second fitted portion 62 fitted in the fixing hole 6w, more specifically, a part of the second fitted portion 62 on the base portion 40a side relative to the protruding end portion 40b in the longitudinal direction N is kept being fitted to the outer circumferential surface 40g of the wall portion 40 and does not deform in the radial direction K.

Therefore, it is possible to prevent a gap from appearing between the second fitted portion 62 and the exterior case 6k.

Thus, it is possible to provide the endoscope 1 having a configuration capable of, even if the cover member 60 moves accompanying a tilt of the operation lever 20, preventing a gap from appearing between the exterior case 6k of the operation portion 6 and the second fitted portion 62 of the cover member 60.

Note that though the endoscope has been shown as an example of a medical apparatus in the embodiment described above, a medical apparatus is not limited to the endoscope. It goes without saying that the present embodiment is applicable to other medical apparatuses having a bending operation mechanism 10 with a configuration similar to the configuration of the present embodiment in an operation portion 6.

What is claimed is:

1. A medical apparatus comprising:
   an operation portion configured to be grasped by an operator;
   an annular wall portion including a base portion connectedly provided to an exterior case of the operation portion and a protruding end portion protrudingly provided from the base portion by a predetermined height;
   an operation lever extended outside the operation portion from inside the operation portion in an area covered by the wall portion and configured so that the operator can perform a tilt operation to the operation portion;
   a cover including a first fitted portion fitted to the operation lever, a deforming portion connectedly provided to the first fitted portion and configured to deform accompanying a tilt of the operation lever, and a second fitted portion connectedly provided to the deforming portion, an inner circumferential surface of the second fitted portion being fitted to an outer circumferential surface of the wall portion; and
   an elastic member formed of rubber including a contact portion in contact with an outer circumferential surface of the second fitted portion, the contact portion being fixed to the exterior case and being deformed to press the outer circumferential surface of the second fitted portion;
   wherein the contact portion of the elastic member tapers off from the base portion side toward the protruding end portion side and has a triangular cross section.

2. The medical apparatus according to claim 1, wherein watertightness of the cover against the wall portion is secured at the second fitted portion.

3. The medical apparatus according to claim 2, further comprising a seal formed on the second fitted portion, the seal being configured to secure the watertightness between the contact portion and the wall portion.

4. The medical apparatus according to claim 3, wherein the seal is thickest at an end of the second fitted portion.

5. The medical apparatus according to claim 1, wherein the contact portion of the elastic member is in contact with the outer circumferential surface of the second fitted portion on a side of the base portion relative to the protruding end portion of the wall portion and the elastic member presses the second fitted portion against the wall portion.

6. A medical apparatus comprising:
an operation portion configured to be grasped by an operator;
an annular wall portion including a base portion connectedly provided to an exterior case of the operation portion and a protruding end portion protrudingly provided from the base portion by a predetermined height;
an operation lever extended outside the operation portion from inside the operation portion in an area covered by the wall portion and configured so that the operator can perform a tilt operation to the operation portion;
a cover including a first fitted portion fitted to the operation lever, a deforming portion connectedly provided to the first fitted portion and configured to deform accompanying a tilt of the operation lever, and a second fitted portion connectedly provided to the deforming portion, an inner circumferential surface of the second fitted portion being fitted to an outer circumferential surface of the wall portion;
an elastic member formed of rubber including a contact portion in contact with an outer circumferential surface of the second fitted portion, the contact portion being fixed to the exterior case and being deformed to press the outer circumferential surface of the second fitted portion; and
a rigid body at least partially disposed in the elastic member such that the rigid body presses the contact portion of the elastic member against the second fitted portion of the cover and the second fitted portion presses against the outer circumferential surface of the wall portion.

7. The medical apparatus according to claim 1, wherein the rigid body is integrally formed with the elastic member.

* * * * *